(12) United States Patent
Wu et al.

(10) Patent No.: US 7,820,399 B2
(45) Date of Patent: Oct. 26, 2010

(54) METHODS FOR CHARACTERIZING GLYCOSYLATION SITES

(75) Inventors: Zhigang Wu, Santa Clara, CA (US); Mohan Srinivasan, Cupertino, CA (US)

(73) Assignee: Medarex, Inc., Princeton, NJ (US)

( * ) Notice: Subject to any disclaimer, the term of this patent is extended or adjusted under 35 U.S.C. 154(b) by 344 days.

(21) Appl. No.: 12/152,906

(22) Filed: May 16, 2008

(65) Prior Publication Data
US 2008/0299678 A1 Dec. 4, 2008

Related U.S. Application Data

(60) Provisional application No. 60/932,710, filed on Jun. 1, 2007.

(51) Int. Cl.
*G01N 33/53* (2006.01)
*G01N 33/543* (2006.01)

(52) U.S. Cl. .................. 435/7.21; 435/7.1; 436/501; 436/518; 422/50; 422/60; 424/9.1

(58) Field of Classification Search .............. None
See application file for complete search history.

(56) References Cited

FOREIGN PATENT DOCUMENTS

JP       07083922       *   3/1995

OTHER PUBLICATIONS

Mathov et al. (Molecular Immunology, vol. 32, No. 14/15, pp. 1123-1130, 1995).*

* cited by examiner

*Primary Examiner*—Lisa V Cook
(74) *Attorney, Agent, or Firm*—Lahive & Cockfield, LLP; Jane E. Remillard, Esq.; Jeanne M. DiGiorgio, Esq.

(57) ABSTRACT

The present invention provides methods for isolating and characterizing the glycosylation sites of a glycoprotein, such as a glycosylated antibody. In particular, the methods employ affinity capture, liquid chromatography, and mass spectrometry to determine, for example, the location of the glycopeptide, the heterogeneity of the glycan attached to the glycopeptide, the mass of the glycopeptide, and/or the peptide sequence.

20 Claims, 3 Drawing Sheets

METHODS FOR CHARACTERIZING GLYCOSYLATION SITES

BACKGROUND OF THE INVENTION

Glycosylation is a posttranslational modification of a protein, such as an antibody, which adds linear or branched chains of monosaccharide units (i.e., glycans) to the protein. Glycosylation creates a vast repertoire of structural and functional diversity on proteins. For example, the culture conditions, choice of expression systems, and the conformation of the antibodies introduce a high degree of structural and sequence heterogeneity in the glycosylation of antibodies. Glycosylation of therapeutic antibodies produced in mammalian expression systems occurs in the constant region (Fc), as well as the heavy and light chain variable regions (Fab), and can significantly modify antibody functions, such as Fc receptor binding, complement activation, and antigen binding affinity.

For antibody product development the identification of the location of the constant and variable region glycans and a complete characterization of their heterogeneity is essential. Specifically, the antibody glycosylation pattern must be controlled during biopharmaceutical production to maintain the efficacy and safety of the therapeutic. The current methods for the characterization of glycopeptides are laborious and are not capable of identifying the location of the constant and variable region glycans of an antibody, particularly when the sequence of the antibody is unknown. Therefore, more efficient methods are needed.

SUMMARY OF THE INVENTION

The present invention provides methods for isolating glycopeptides derived from a glycosylated protein, such as an antibody, and characterizing at least one glycosylation site within the glycopeptides (e.g., determining the location of a glycosylation site as being within the constant region and/or the heavy or light chain variable region of an antibody). In a particular embodiment, the sequence of the glycoprotein or antibody is unknown.

Accordingly, in one embodiment, the method includes the steps of (i) chemically or enzymatically cleaving the glycoprotein, such as, a glycosylated antibody, (using, e.g., trypsin, LysC, GluC, or AspN) to generate a mixture of glycopeptides and peptides, (ii) contacting the mixture with a carbohydrate binding moiety, such as, a lectin (e.g., concanavalin A (ConA), wheat germ agglutinin (WGA), *Aleuria aurantia* lectin (AAL), *Anguilla anguilla* agglutinin (AAA), SNA1 (*Sambucus nigra*), *Helix pomatia* agglutinin, or combinations thereof) bound to a solid support, and (iii) isolating the glycopeptides bound to the carbohydrate binding moiety.

In another embodiment, the method further includes the step of separating the isolated glycopeptides using high performance liquid chromatography (HPLC) and using the elution times of the glycopeptides to determine the location of the glycopeptide within the glycoprotein or antibody. For example, the glycopeptides can be identified as being located within the constant region or the variable regions of the antibody based on the elution times.

In another embodiment, the method of the present invention includes the step of analyzing the isolated glycopeptides by mass spectrometry (MS), such as by electrospray ionization (ESI), matrix-assisted laser desorption ionization (MALDI) or atmospheric pressure ionization (APCI). In another embodiment, the method further includes the step of determining the presence of a marker ion indicative of the presence of a glycopeptide (e.g., HexNAc, Hexose, Sialic Acid or Hexose-HexNAc ions) and identifying the presence of a glycopeptide. The presence of the marker ion further defines the location of the glycopepetides, e.g., as being located within the constant region and/or the variable regions of the glycosylated antibody.

In another embodiment, the step of analyzing the isolated glycopeptides by MS is used to determine the heterogeneity of the glycan attached to the isolated glycopeptide, the glycopeptide mass, and/or the peptide sequence.

In another embodiment, the method of the present invention includes the step of reducing and alkylating the glycoprotein before cleaving the glycoprotein, at least one wash step, the step of eluting the glycopeptides from the carbohydrate binding moiety using a molecule that competes with the glycopeptides for binding to the carbohydrate binding moiety (e.g., methyl mannopyranoside), and/or the step of desalting.

Other features and advantages of the instant invention will be apparent from the following detailed description and examples which should not be construed as limiting. The contents of all references, Genbank entries, patents and published patent applications cited throughout this application are expressly incorporated herein by reference.

DETAILED DESCRIPTION OF THE INVENTION

Figure 1:
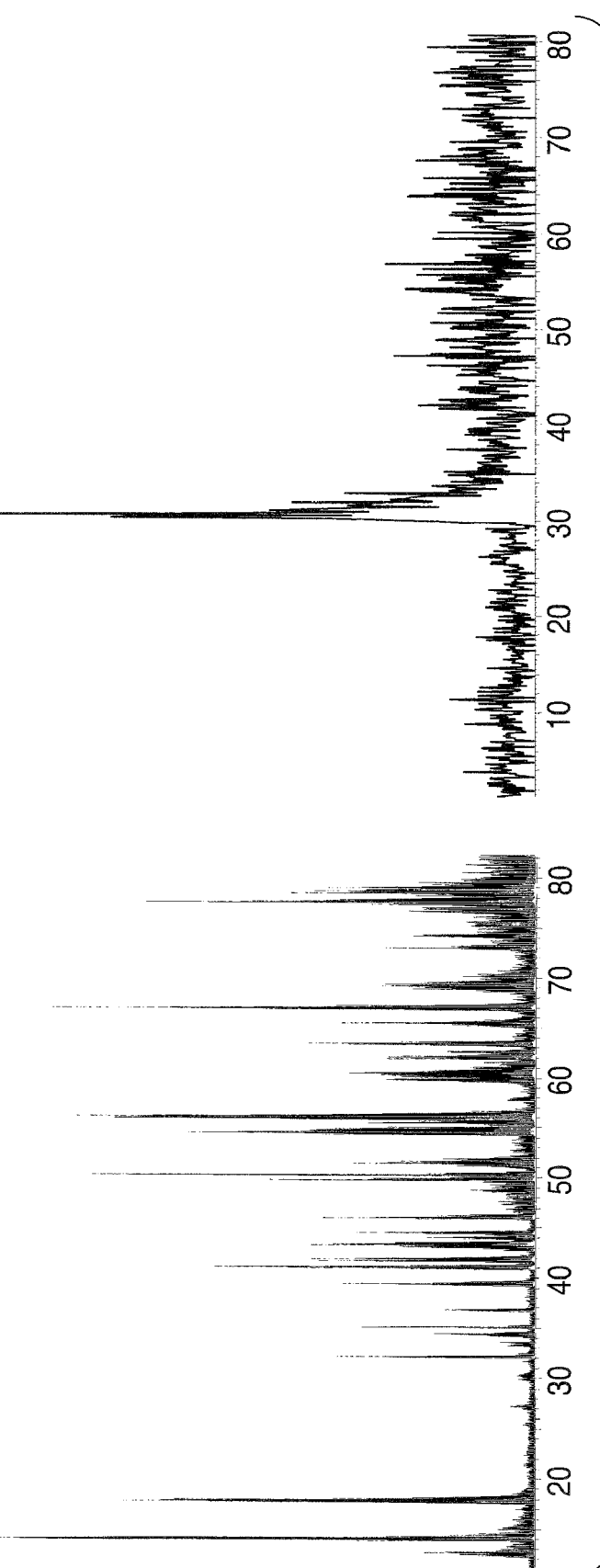
FIG. 1 shows (A) the full scan of a monoclonal antibody digest without lectin enrichment of the glycopeptides and (B) the in-source collision scan after glycopeptide enrichment using lectin capture. Marker ions such as HexNAc$^+$ (204 Da) can be used to locate glycopeptide elution time.
Figure 1:
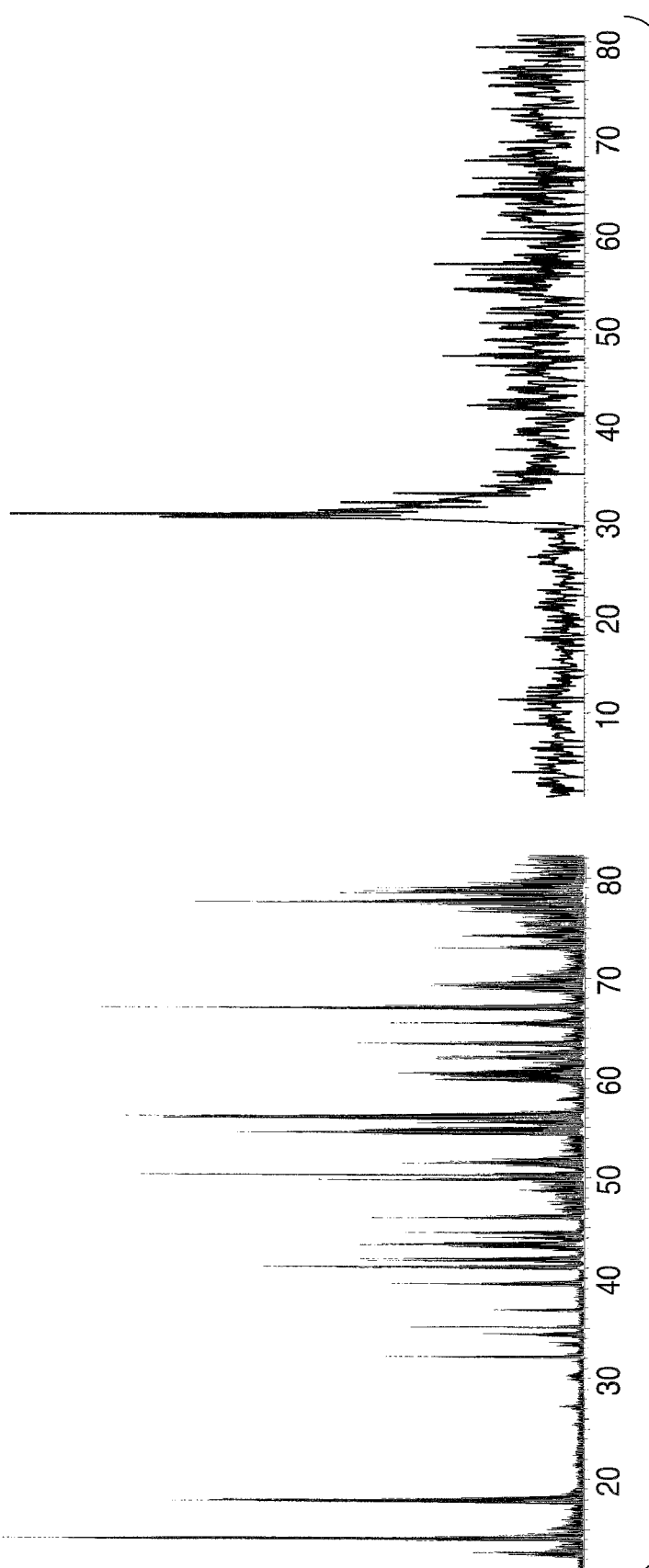

The present invention provides methods for isolating and characterizing the glycosylation sites within a glycoprotein, e.g., a glycosylated antibody. In certain embodiments, by employing techniques such as affinity capture, high performance liquid chromatography, and/or mass spectrometry, the location of a glycosylation site within an antibody (e.g., a glycosylation site within the constant region and/or within the heavy or light chain variable region) is identified without knowledge of the antibody sequence. Further characterization of the glycosylation sites based on the methods of the present invention include determination of the heterogeneity of the glycan attached to the antibody, the glycopeptide mass, and/or the peptide sequence. The methods of the present invention are particularly useful in the development of therapeutic antibodies where glycosylation modifies the functions and efficacy of the antibody and, thus, knowledge of the glycosylation sites or the heterogeneity of glycosylation enables more efficient manufacturing protocols and facilitates selection of a candidate antibody. Since the glycopeptides of the constant and variable domains of the antibodies are separated by HPLC, the carbohydrates corresponding to the different glycosylation sites are identified separately. The current methods in the art do not allow the separate identification of the sugars belonging to the different glycosylation sites.

Definitions

As used herein, "protein" refers generally to peptides and proteins having at least 5 amino acids or more which are linked together by peptide bonds. A protein is typically a complex polypeptide, which can be an antibody, receptor, ligand fusion protein (which comprise at least a portion of two or more polypeptides that are not fused in their natural state), fragments and variants thereof etc. A protein purified according to a method of the present invention can be from any organism (prokaryotic or eukaryotic), particularly from mammals.

The term "glycoslyation" refers to the process or result of adding saccharides to proteins and lipids, thus, forming "glycoproteins," "glycopeptides," or "glycolipids." The process is one of four principal co-translational and post-translational modification steps in the synthesis of membrane and secreted proteins and the majority of proteins synthesized in the rough endoplasmic reticulum undergo glycosylation. Glycosylation is an enzyme-directed site-specific process. Two types of glycosylation exist: N-linked glycosylation to the amide nitrogen of asparagine side chains and O-linked glycosylation to the hydroxy oxygen of serine and threonine side chains.

The linear or branched chains of monosaccharide units which form the carbohydrate portion of the glycopeptide are known as glycans and serve various functions. For example, glycosylation may be required for proper folding and polysaccharides linked at the amide nitrogen of asparagine in the protein confer stability on some secreted glycoproteins. Glycosylation also plays a role in cell-cell adhesion.

The term "antibody" is used in the broadest sense to include monoclonal antibodies, polyclonal antibodies, multispecific antibodies (e.g., bispecific antibodies), immunoadhesins and antibody fragments. An antibody or fragment can be modified such as defucosylated antibody. An antibody can be directed against an "antigen" of interest, such as a polypeptide, which may be a biologically relevant therapeutic target, or a non-polypeptide antigen (e.g., such as tumor-associated glycolipid antigens; see U.S. Pat. No. 5,091,178). Preferably, the antigen is a biologically important polypeptide and administration of the antibody to a mammal suffering from a disease or disorder can result in a therapeutic benefit in that mammal. Polypeptide antigens include transmembrane molecules (e.g., receptor) and ligands such as growth factors. Exemplary antigens include those polypeptides discussed above. The preparation of antigens for generating antibodies and antibody production are well known in the art. Soluble antigens, or fragments thereof optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule.

An "antibody fragment" includes at least a portion of a full length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g.,. human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530, 101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-Mouse® (Medarex, Inc., Princeton, N.J.) which has a human heavy chain transgene and a human light chain transchromosome (see WO 02/43478), Xenomouse® (Abgenix, Inc., Fremont Calif.; described in, e.g., U.S. Pat. Nos. 5,939,598; 6,075,181; 6,114, 598; 6,150,584 and 6,162,963 to Kucherlapati et al.), and HuMAb-Mouse® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569, 825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The term "hypervariable region" is used to describe the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; see Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues.

As used herein, the term "immunoadhesin" designates antibody-like molecules which combine the "binding domain" of a heterologous "adhesin" protein (e.g., a receptor, ligand or enzyme) with the effector functions of an immunoglobulin constant domain. Structurally, an immunoadhesin comprises a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains, since immunoadhesins comprising these regions can be purified by Protein A chromatography (Lindmark et al., J. Immunol. Meth. 62:1-13 (1983)).

Immunoadhesins can be purified according to methods of the present invention.

A "peptibody" refers to molecules comprising an Fc domain and at least one peptide. Such peptibodies may be multimers or dimers or fragments thereof, and they may be derivatized. Peptibodies are described in greater detail in US Patent Publication No. 20040214190, WO 00/24782 and WO 01/83525, which are incorporated herein by reference in their entireties.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., PNAS (USA) 88:4723-4727 (1991) and Chamow et al., J. Immunol. 153:4268 (1994).

The term "carbohydrate binding moiety" refers to a chemical or enzyme that reversibly binds to one or more carbohydrates. The carbohydrate binding moiety may be attached to a solid support or resin and used as an affinity column. An example of a carbohydrate binding moiety is a lectin.

The term "lectin" refers to a class of proteins that bind to carbohydrates. Examples of lectins for use in the present invention include concanavalin A (ConA), wheat germ agglutinin (WGA), *Aleuria aurantia* lectin (AAL), *Anguilla anguilla* agglutinin (AAA), SNAL (*Sambucus nigra*), *Helix pomatia* agglutinin, or combinations thereof.

The term "marker ion" refers to low a molecular weight ion that is used to identify the presence of particular in compound, for example a peptide or protein, in a sample, subjected to mass spectrometry (e.g., glycosylation or phosphorylation). Marker ions used in the present invention may include m/z 163 (Hexose), 204 (HexNAc), 274 (sialic acid-$H_2O$), 292 (sialic acid), and 366 (Hexose-HexNAc).

The term "mass spectrometer" refers to an instrument which can measure the masses of atoms and molecules through ionization. The ionization methods of the present invention include, but are not limited to electrospray ionization (ESI), matrix-assisted laser desorption ionization (MALDI) or atmospheric pressure ionization (APCI). There are many types of mass spectrometry systems which can be used in the methods of the present invention including, but not limited to single or triple quadrupole mass spectrometers, ion trap mass spectrometers, time of flight mass spectrometers.

As used herein, a "mixture" comprises a polypeptide of interest (for which purification is desired) and one or more contaminant, i.e., impurities. The mixture can be obtained directly from a host cell or organism producing the polypeptide. Without intending to be limiting, examples of mixtures that can be purified according to a method of the present invention include harvested cell culture fluid, cell culture supernatant and conditioned cell culture supernatant. A mixture that has been "partially purified" has already been subjected to a chromatography step, e.g., non-affinity chromatography, affinity chromatography, etc. A "conditioned mixture" is a mixture, e.g., a cell culture supernatant that has been prepared for a chromatography step used in a method of the invention by subjecting the mixture to one or more of buffer exchange, dilution, salt addition, pH titration or filtration in order to set the pH and/or conductivity range and/or buffer matrix to achieve a desired chromatography performance. A "conditioned mixture" can be used to standardize loading conditions onto the first chromatography column. In general, a mixture can be obtained through various separation means well known in the art, e.g., by physically separating dead and viable cells from other components in the broth at the end of a bioreactor run using filtration or centrifugation, or by concentration and/or diafiltration of the cell culture supernatant into specific ranges of pH, conductivity and buffer species concentration.

The terms "impurity" and "contaminant", and grammatical variations thereof, are used interchangeably to mean any material, other than the protein of interest for which it is desirable to have removed from a composition containing the protein of interest. Contaminants include, but are not limited to, any biological macromolecule such as host cell proteins (e.g., CHOPs), polypeptides other than the protein of interest, nucleic acids (e.g., DNA and RNA), lipids, saccharides, endotoxins, bacteria or other microorganisms such as yeast, media components, and any molecule that is part of an adsorbent used in chromatography which may leach into a sample during chromatography, and the like.

The term "protein of interest" and "target protein" are used interchangeably to refer to a protein, as described above, e.g., an antibody, for which it is desirable to purify and characterize from a mixture according to a method of the present invention.

The term "host cell protein", or "HCP", refers to any of the proteins derived from the metabolism (intra and extra-cellular) of the host cell that expresses the target protein, including any proteins expressed from the genome of the host cell or proteins that are recombinantly expressed, and which are not considered the target protein. The host cell can be any cell that is capable of expressing the target protein, particularly mammalian (e.g., CHO and murine myeloma cell lines such as NSO), insect bacterial, plant and yeast cell lines. In a particular embodiment of the invention, the HCP is a "Chinese hamster ovary cell protein", or "CHOP", which refers to any of the host cell proteins ("HCP") derived from a Chinese hamster ovary ("CHO") cell culture. The HCP is present generally as an impurity in a cell culture medium or lysate [(e.g., a harvested cell culture fluid ("HCCF")], which contains the protein of interest. The amount of HCP present in a mixture comprising a protein of interest provides a measure of the degree of purity for the protein of interest. Typically, the amount of HCP in a protein mixture is expressed in parts per million relative to the amount of the protein of interest in the mixture.

The term "parts per million" or "ppm" are used interchangeably herein to refer to a measure of purity of the protein of interest purified by a method of the invention. The units ppm refer to the amount of HCP in nanograms/milliliter per protein of interest in milligrams/milliliter, where the proteins are in solution (i.e., as described in an Example infra, HCP ppm=(CHOP ng/ml)/(protein of interest mg/ml)). Where the proteins are dried, such as by lyophilization, ppm refers to (HCP ng)/(protein of interest mg).

The term "purify", and grammatical variations thereof, is used to mean the removal, whether completely or partially, of at least one impurity from a mixture containing the protein and one or more impurities, which thereby improves the level of purity of the protein in the composition (i.e., by decreasing the amount (ppm) of impurity(ies) in the composition).

The term "characterize", and grammatical variations thereof, is used to mean to define the features (e.g., structural or functional) of a protein of interest. According to the present invention, characterization is accomplished by, for example, defining the location of an antibody fragment within a glycosylated antibody (e.g., as being located within the constant region and/or the variable regions of the glycosylated antibody), the heterogeneity of the glycan attached to the isolated antibody fragment, the glycopeptide mass, and/or the peptide sequence.

As used herein, the term "isolate", and grammatical variations thereof, refers to the separation of a purified protein of interest from additional substances, e.g., from a column or resin used to purify the protein of interest, in order to achieve a homogenous composition, which contains the protein of interest substantially free from contaminants, impurities and other substances.

The term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as p1, hydrophobicity, size and structure, under particular buffering conditions of the process. Use of the term "chromatography" includes column and membrane types.

An "adsorbent" is any solid and fixed substance capable of adsorbing another substance to its surface by adhesion by either direct interaction with the molecule of interest or interaction with compounds that are attached to the adsorbent. Adsorbents that are useful in various types of chromatography are well known in the art and are readily available through commercial sources.

The term "affinity chromatography," "protein affinity chromatography," and "affinity capture" are used interchangeably to refer to a protein separation technique in which a protein of interest is reversibly and specifically bound to a biospecific ligand, usually as a combination of spatial complementarity and one or more types of chemical interactions, e.g., electrostatic forces, hydrogen bonding, hydrophobic forces, and/or van der Waals forces at the binding site. These interactions are not due to the general properties of the molecule such as isoelectric point, hydrophobicity or size but are a result of specific interactions from the molecule of interest and the ligand such as the hydrophobic and precise protein domain fit for protein A and antibody interactions, for example. Protein A is an example of an adsorbent, which can be fixed to a solid support, e.g., Sepharose, for binding molecules that contain an Fc region. See Ostrove (1990) in Guide to Protein Purification, Methods of Enzymology 182: 357-379, which is incorporated herein by reference in its entirety.

Any ligand can be used to purify its respective specific binding protein. Preferably, the biospecific ligand is covalently attached to a chromatographic solid phase material and is accessible to the protein of interest (e.g., antibody, enzyme, or receptor protein) in solution as the solution contacts the chromatographic solid phase material. The protein of interest retains its specific binding affinity for the biospecific ligand (antigen, substrate, cofactor, carbohydrate, or hormone, for example) during the chromatographic steps, while other solutes and/or proteins in the mixture do not bind appreciably or specifically to the ligand. Binding of the protein of interest to the immobilized ligand allows contaminating proteins and other impurities to be passed through the chromatographic medium while the protein of interest remains specifically bound to the immobilized ligand on the solid phase material. The specifically bound protein is then removed form the immobilized ligand with low pH, high pH, low salt, high salt, competing ligand, or the like, and passes through the chromatographic column with the elution buffer. Contaminating proteins having a lower relative concentration to the protein of interest, and other types of contaminants such as nucleic acids and endotoxin, that were earlier allowed to pass through the column, may also be present.

The terms "specific binding" and "binding specificity", and grammatical variations thereof, describe the generally specific and reversible interactions between a protein of interest and a ligand requiring the combined effects of spatial complementarity of protein and ligand structures at a binding site coupled with one or more type of electrostatic forces, hydrogen bonding, hydrophobic forces, and/or van der Waals forces at the binding site. The ligand should have chemically modifiable groups which allow it to be attached to the matrix without destroying its binding activity. The ligand should ideally have an affinity for the binding substance in the range $10^{-4}$ to $10^{-8}$ M in free solution. The greater the spatial complementarity and the stronger the other forces at the binding site, the greater will be the binding specificity of a protein for its respective ligand. Non-limiting examples of specific binding include antibody-antigen binding, enzyme-substrate binding, enzyme-cofactor binding, metal ion chelation, DNA binding protein-DNA binding, regulatory protein-protein interactions, and the like.

The terms "non-affinity chromatography" and "non-affinity purification" refer to a purification step which does not use affinity chromatography, but rather requires a non-specific binding interaction between a solute (e.g., protein of interest) and the adsorbent matrix.

The term "non-specific binding" as used herein, refers to the interactions between a protein of interest and a ligand or other compound bound to a solid phase matrix through non-specific interactions, e.g., through electrostatic forces, hydrogen bonding, hydrophobic forces, and/or van der Waals forces at an interaction site, but lacking the structural complementarity that enhances the effects of the non-structural forces such as in affinity (specific) binding. Examples of chromatography processes that rely on non-specific binding, rather than affinity, include ionic exchange chromatography (e.g., anionic and cationic exchange) and hydrophobic charge induction chromatography.

The term "solid phase" is used to mean any non-aqueous matrix to which one or more ligands can adhere or alternatively, in the case of size exclusion chromatography, it can refer to the gel structure of a resin. The solid phase can be any matrix capable of adhering ligands in this manner, e.g., a purification column, a discontinuous phase of discrete particles, a membrane, filter, gel, etc. Examples of materials that can be used to form the solid phase include polysaccharides (such as agarose and cellulose) and other mechanically stable matrices such as silica (e.g., controlled pore glass), poly(styrenedivinyl)benzene, polyacrylamide, ceramic particles and derivatives of any of these. The present invention is not limited to any particular solid phase material for use in a chromatography step, and those having ordinary skill in the art will be able to select appropriate solid phase material for use in the present invention.

A "buffer" used in the present invention is a solution that resists changes in pH by the addition of acid or base by the action of its acid-base conjugates components. Various buffers can be employed in a method of the present invention depending on the desired pH of the buffer and the particular step in the purification process [see Buffers. A Guide for the Preparation and Use of Buffers in Biological Systems, Gueffroy, D., ed. Calbiochem Corporation (1975)]. Non-limiting examples of buffer components that can be used to control the pH range desirable for a method of the invention include acetate, citrate, histidine, phosphate, ammonium buffers such as ammonium acetate, succinate, MES, CHAPS, MOPS, MOPSO, HEPES, Tris, and the like, as well as combinations of these TRIS-malic acid-NaOH, maleate, chloroacetate, formate, benzoate, propionate, pyridine, piperazine, ADA, PIPES, ACES, BES, TES, tricine, bicine, TAPS, ethanolamine, CHES, CAPS, methylamine, piperidine, 0-boric acid, carbonic acid, lactic acid, butaneandioic acid, diethylmalonic acid, glycylglycine, HEPPS, HEPPSO, imidazole, phenol, POPSO, succinate, TAPS, amine-based, benzylamine, trimethyl or dimethyl or ethyl or phenyl amine, ethylenediamine, or mopholine Additional components (additives) can be present in a buffer as needed, e.g., salts can be used to adjust buffer ionic strength, such as sodium chloride, sodium sulfate and potassium chloride; and other additives such as amino acids (such as glycine and histidine), chaotropes (such as urea), alcohols (such as ethanol, mannitol, glycerol, and benzyl alcohol), detergents (see supra.), and sugars (such as sucrose, mannitol, maltose, trehalose, glucose, and fructose). The buffer components and additives, and the concentrations used, can vary according to the type of chromatography practiced in the invention.

The pH and conductivity of the buffers can vary depending on which step in the purification process the buffer is used. Any suitable buffer at a pH compatible with the selected ligand and resin/membrane can be used for purifying the protein of interest, such as the buffers described above.

A "sanitization" solution is typically used to clean the resin used in column chromatography by removing any bound contaminants, e.g., those of biological origin, prior to the purification process. Any desirable buffer could be used for this purpose provided it is compatible with the particular column and resin selected according to a method of the invention. Preferably, the pH of the sanitization solution is high, e.g., pH 10 or greater, more preferably pH 11 or greater, and still more preferably pH 12 or greater; alternatively, the pH of the sanitization solution can be low, e.g. pH 4 or less, more preferably pH 3 or less. In a particular embodiment, a resin used in a method of the invention is cleaned using a sanitization solution that includes 1N NaOH, pH$\geq$12.

An "equilibration buffer" is used to adjust the pH and conductivity of the chromatography medium, e.g., a resin or membrane, prior to loading the resin with the mixture containing the protein of interest for purification. Suitable buffers that can be used for this purpose are well known in the art, e.g., such as buffers described above, and include any buffer at pH that is compatible with the selected resin used in the chromatography step for purifying the protein of interest.

The equilibration buffer has a conductivity and/or pH such that the polypeptide of interest is bound to the resin or such that the protein of interest flows through the column while one or more impurities bind to the column. In a particular embodiment, equilibration is completed when the pH and conductivity of the chromatography medium are within ±0.2 and ±0.4 mS/cm of the equilibrating buffer, respectively, more preferably within ±0.1 and ±0.2 mS/cm of the equilibrating buffer, respectively.

A "loading buffer" is used to load the mixture containing the protein of interest onto the column. It shall be appreciated that if a membrane is used as the chromatography medium then the loading buffer is simply contacted with the membrane according to conventional methods used in the art. Any appropriate buffered solution can be used as the loading buffer. In a particular embodiment, the loading buffer is a phosphate or TRIS buffer. Suitable buffers for use as a loading buffer are well known in the art, e.g., such as those described above.

The terms "wash buffer" or "post load wash", as used herein, refer to a buffer used to remove impurities from a chromatography resin (e.g., when using a column) prior to eluting the protein of interest. The term "washing", and grammatical variations thereof, is used to describe the passing of an appropriate wash buffer through or over the chromatography resin. If desirable, the wash, equilibration and loading buffers can be the same. If desirable, the wash buffer can contain a detergent, such as a polysorbate. It is important to select pH and conductivity of the wash buffer to remove HCPs and other contaminants without significantly eluting the protein of interest. The pH and conductivity conditions described above for equilibration and loading buffers are sufficient to achieve this goal.

The term "elution buffer", as used herein, refers to a buffer used to elute the protein of interest from the resin. The term "elute", and grammatical variations thereof, refers to the removal of a molecule, e.g., polypeptide of interest, from a chromatography material by using appropriate conditions, e.g., altering the ionic strength or pH of the buffer surrounding the chromatography material, by addition of a competitive molecule for the ligand, by altering the hydrophobicity of the molecule or by changing a chemical property of the ligand (e.g., charge), such that the protein of interest is unable to bind the resin and is therefore eluted from the chromatography column. The term "eluate" refers to the effluent off the column containing the polypeptide of interest when the elution is applied onto the column. After elution of the polypeptide of interest the column can be regenerated, sanitized and stored as needed. The pH and conductivity of the elution buffer are selected such that the protein of interest is eluted from the resin used in the process.

If desired, additional solutions may be used to prepare the column for reuse. For example, a "regeneration solution" can be used to "strip" or remove tightly bound contaminants from a column used in the purification process. Typically, the regeneration solution has a conductivity and pH sufficient to remove substantially any remaining impurities and protein of interest from the resin.

Description of the Process

In a method of the present invention, affinity capture using a carbohydrate binding moiety (e.g., a lectin) is used to purify a protein of interest, such as a chemically or enzymatically cleaved glycosylated antibody. The isolated antibody fragments (i.e., glycopeptides) are further separated using high performance liquid chromatography (HPLC), wherein the elution times of the antibody fragments are used to determine the location of the glycosylation site within the antibody (e.g., located within the constant region and/or the variable regions of the antibody). In another embodiment, the sequence of the glycoprotein or antibody is unknown.

The protein of interest can be produced or expressed by living host cells that have been genetically engineered to produce the protein. Methods of genetically engineering cells to produce proteins are well known in the art. See, e.g., Ausabel et al., eds. (1990), Current Protocols in Molecular Biology (Wiley, New York) and U.S. Pat. Nos. 5,534,615 and 4,816,567, each of which is specifically incorporated herein by reference. Such methods include introducing nucleic acids that encode and allow expression of the protein into living host cells. These host cells can be bacterial cells, fungal cells, or, preferably, animal cells grown in culture. Bacterial host cells include, but are not limited to E. coli cells. Examples of suitable E. coli strains include: HB101, DH5α, GM2929, JM109, KW251, NM538, NM539, and any E. coli strain that fails to cleave foreign DNA. Fungal host cells that can be used include, but are not limited to, Saccharomyces cerevisiae, Pichia pastoris and Aspergillus cells. A few examples of animal cell lines that can be used are CHO, VERO, DXB11, BHK, HeLa, Cos, MDCK, 293, 3T3, NS0 and W1138. New animal cell lines can be established using methods well know by those skilled in the art (e.g., by transformation, viral infection, and/or selection). In particular embodiments, the protein of interest is produced in a CHO cell (see, e.g., WO 94/11026). Various types of CHO cells are known in the art, e.g., CHO-K1, CHO-DG44, CHO-DXB11, CHO/dhfr⁻ and CHO-S. A host cell that has been engineered with nucleic acid encoding the protein of interest can be cultured under conditions well known in the art that allow expression of the protein.

Preparation of a mixture for protein purification from cellular debris initially depends on the manner of expression of the protein. Some proteins are caused to be secreted directly from the cell into the surrounding growth media, while other proteins are retained intracellularly. For such proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

When using recombinant techniques, the protein of interest can be produced intracellularly, in the periplasmic space, or directly secreted into the medium. A method of the invention does not rely on any particular methodology to remove cellular debris. Any method can be employed by the skilled practitioner to accomplish this. If the protein is produced intracellularly, as a first step, the particulate debris, either host cells or lysed fragments, can be removed, for example, by a centrifugation or filtration step in order to prepare a mixture for purification. If the protein is secreted into the medium, the recombinant host cells may be separated from the cell culture medium by, e.g., tangential flow filtration (TFF) or depth filtration, in order to prepare a mixture for purification.

In another embodiment, once a mixture containing the isolated antibody fragments is obtained and separated, it is analyzed by mass spectrometry (MS), e.g., electrospray ionization (ESI), matrix-assisted laser desorption ionization (MALDI) or atmospheric pressure ionization (APCI). Accordingly, identification of the presence of a glycosylated antibody fragment is determined based on the presence of a marker ion indicative of the presence of a glycopeptide (e.g., HexNAc). Further characterization of the glycosylation site is accomplished by identifying the location of the glycosylation site within the glycoprotein or antibody (e.g., located within the constant region and/or the variable regions of the antibody), the heterogeneity of the glycan attached to the isolated glycopeptide, the glycopeptide mass, and/or the peptide sequence.

In another embodiment, the method of the present invention further includes the step of reducing and alkylating the glycoprotein before cleaving the glycoprotein, at least one wash step, eluting the glycopeptides from the carbohydrate binding moiety using molecule that competes with the glycopeptides for binding to the carbohydrate binding moiety (e.g., methyl mannopyranoside), and/or the step of desalting.

The chromatographic steps of the invention can be carried out by any mechanical means. Chromatography may be carried out in a column. The column may be run with or without pressure and from top to bottom or bottom to top. If desirable, the direction of the flow of fluid in the column may be reversed during a chromatography process according to routine methods well known in the art. Chromatography may also be carried out using a batch process in which the solid support is separated from the liquid used to load, wash, and elute the sample by any suitable means, including gravity, centrifugation, or filtration. Chromatography may also be carried out by contacting the sample with a charged filter that absorbs or retains some molecules in the sample more strongly than others, using the same chemical principles as those described for a chromatography resin. Although steps in the preparation of columns used in the present invention can be tailored to suit the individual needs of the practitioner, the following description is provided as guidance, and those having ordinary skill in the art will appreciate alterations can be made without departing from the spirit of the invention. Columns and membranes are prepared according to the manufacturer's instructions. Prior to purification, columns are typically sanitized using a sanitization solution, and equilibrated using an equilibration buffer. During the sanitization step, typically there is a hold, e.g., for about 15 to 30 minutes, preferably for about 1 hour, after the sanitization solution is applied onto the column in order to clean the resin having any bound contaminants, including contaminants of biological origin. An equilibration buffer is used to equilibrate the column in order to prepare the pH and conductivity of the resin to bind the protein of interest. For example, the column can be considered equilibrated when its pH and conductivity are within ±0.1 and within ±0.2 mS/cm of the pH and conductivity of the equilibrating buffer, respectively.

Once the mixture has been loaded onto the column and the protein of interest is bound to the resin, wash steps using a wash buffer as described are performed to clear contaminants from the column. Optionally, a wash step can be performed at a slower flow rate than for the other wash and elution steps (but is not necessary), e.g., using a flow rate corresponding to several minutes (e.g., 2 to 30 minutes) residence time.

To elute the protein of interest from the column, an appropriate elution buffer is used, as described above, to cause the protein of interest to reverse binding off the column. The type and concentration of buffer, salt, and/or other compound in the buffer composition are such that the protein of interest elutes differentially in relation to the impurity(ies). The appropriate pH and conductivity ranges for loading, wash, and elution buffers can be readily determined by those having ordinary skill in the art such that the protein of interest is recovered during elution. As the protein of interest is removed from the column, it is collected based on formation of a peak from rising $A_{280}$ to falling $A_{280}$. The baseline can be readily determined by one of ordinary skill in the art by measuring the absorbance of the equilibrating buffer at 250-280 nm while the equilibrating buffer passes through the column.

The mass spectrometry of the invention can be carried out by any appropriate mechanical device capable of measuring the mass-to-charge ratio of ions. In general, the device will include an ion source, one or more mass analyzers, and a detector system. The stages within the mass spectrometer are: producing ions from the sample; separating ions of differing masses; detecting the number of ions of each mass produced; collating the data and generating the mass spectrum. For example, a tandem mass spectrometer (MS/MS) instrument or, more generally, a multidimensional mass spectrometer (MS$^n$) instrument coupled with an electrospray or MALDI ion source and ion trap system, can be used to perform the methods of the present invention.

The following Example is provided for purposes of demonstrating the invention, and is not intended to be limiting.

EXAMPLE

Identification of Glycan Structure from Constant and Variable Regions of a Human Monoclonal Antibody Glycopeptide Sample Preparation After reduction and alkylation, the monoclonal antibody was digested overnight with trypsin. The tryptic digest was then incubated with a slurry of lectin beads (ConA and/or WGA) for 15 minutes with shaking to capture glycopeptides from non-glycosylated peptides present in the digest. Lectin beads were loaded into a column and then washed with Tris buffered saline at least 3 times to remove the non-glycosylated peptides. Resin bound glycopeptides were eluted with 100 ul 0.3M methyl mannopyranoside in Tris buffered saline twice. The eluted solution containing glycopeptide mixture was desalted and concentrated to ~20 ul using a C18 ZipTip®D. The sample was eluted from the ZipTip® and loaded onto the LC/MS system.

Liquid Chromatography/Mass Spectrometry

Figure 2:
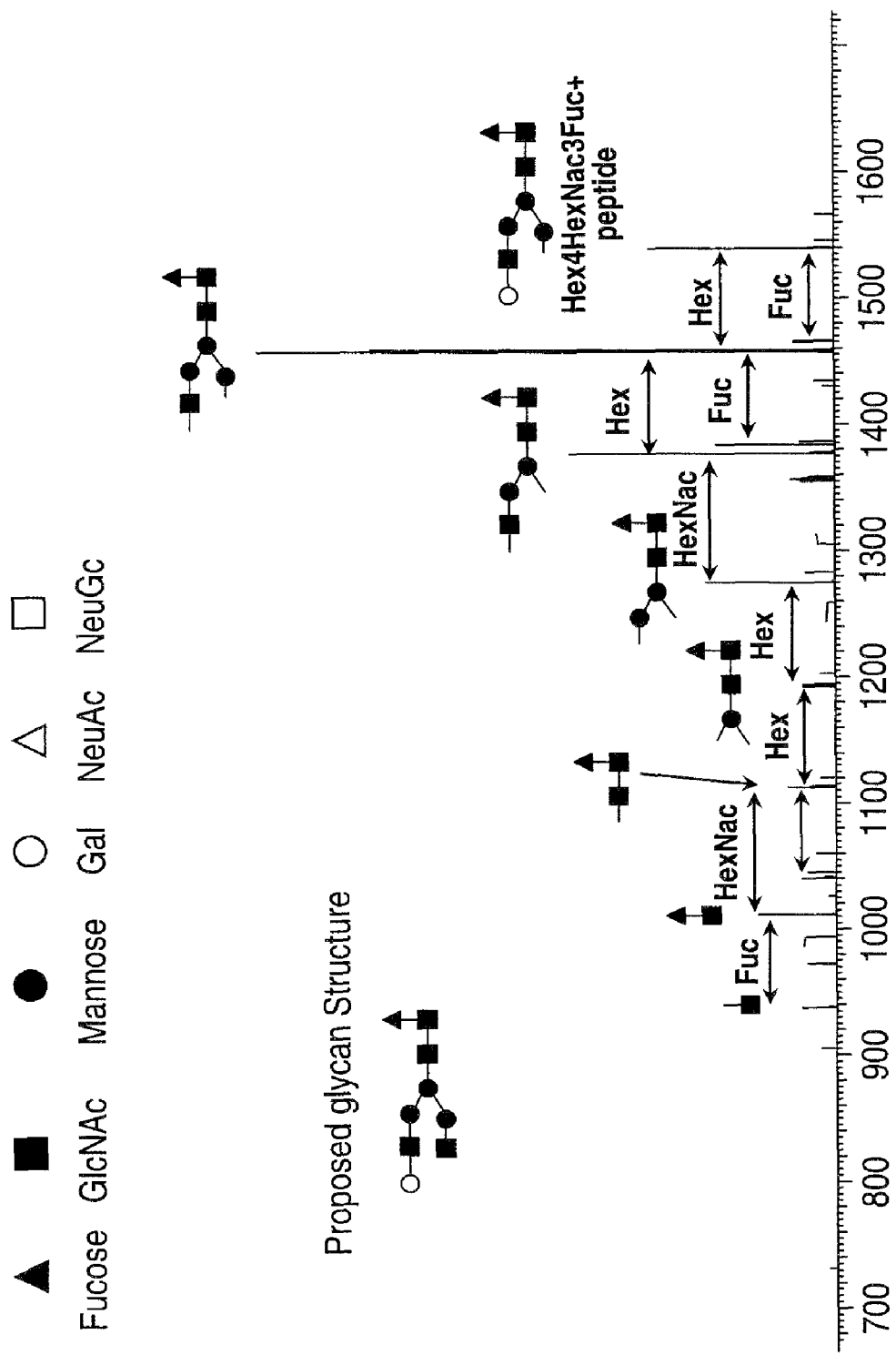
FIG. 2 shows the MS/MS spectrum of glycopeptide showing the suggested glycan structure for a constant Fc region glycopeptide.
Figure 3:
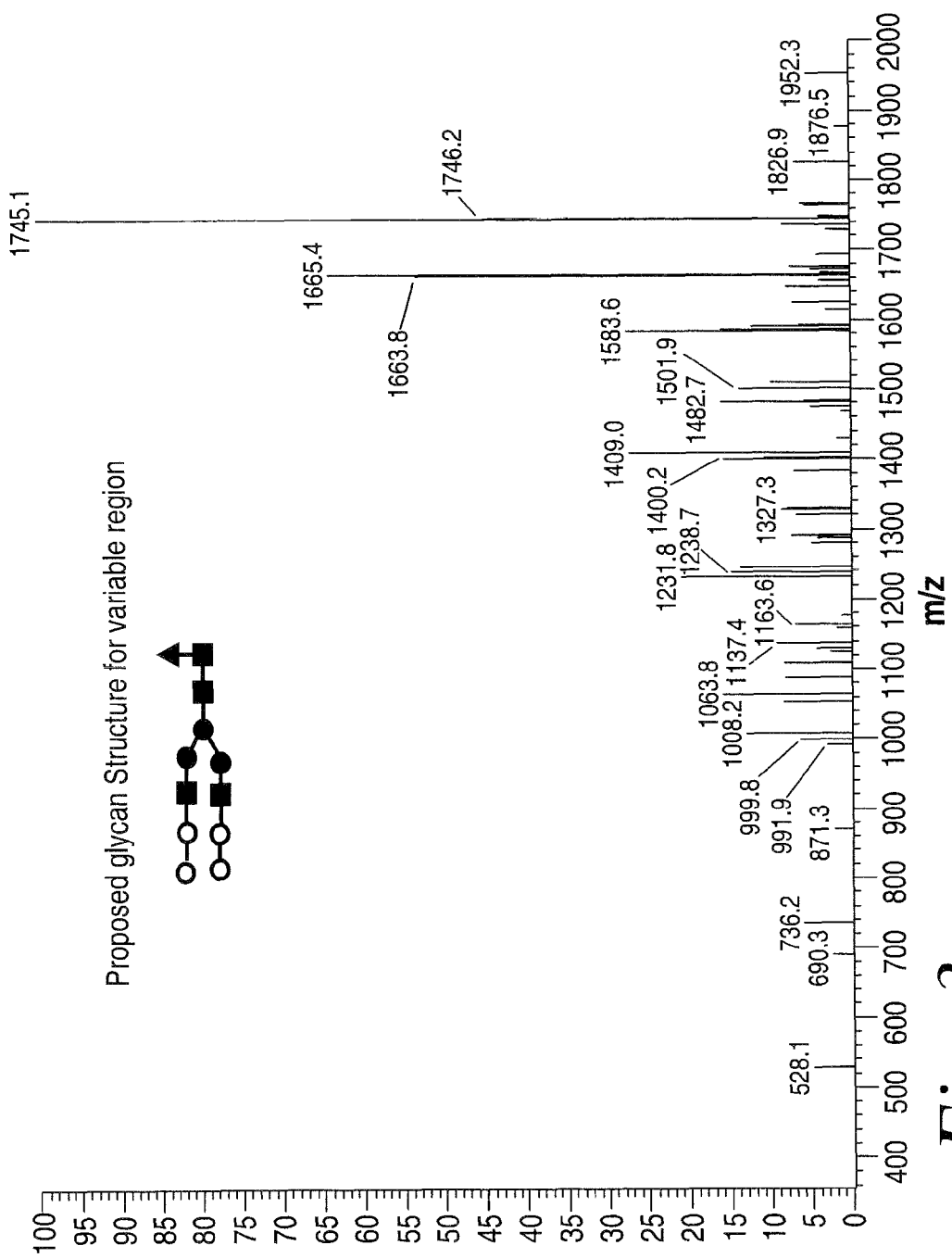
FIG. 3 shows the MS/MS spectrum of glycopeptide showing the suggested glycan structure for a variable Fv region glycopeptide.

HPLC separation were conducted at 0.2 ml/min, using 5% (vol/vol) acetonitrile/water as solvent A and 80% (vol/vol) acetonitrile/water as solvent B. Sample elution was carried out at 100% A for 10 min, followed by a linear increase to 50% B at 70 min. The column was washed with 95% B for 10 min and equilibrated at 100% A for 10 min before the next injection. An in-source ionization method in ion-trap mass spectrometry was used to locate glycopeptides and then tandem mass spectrometry was applied to identify the sequence of the glycan unit attached to the glycopeptide. Five sequenced scans are programmed in the instrumental method. First, an in source fragmentation scan was performed to identify the location of glycopeptides by generating marker ions such as HexNAc at 204 Daltons (FIG. 1B). Sometime marker ion scan might not be evident enough to locate glycopeptides. Therefore, manually checking each possible group of glycopeptides is performed especially for variable region glycosylation. Next, a full mass scan was performed to locate the glycopeptides, followed by a zoom-scan to calculate the mass of the individual glycopeptides. MS/MS was then performed to further characterize the glycan structure. With the aid of a glycan database (GlycoMod), the peptide sequence and glycan mass was determined. Based on MS/MS spectral data, glycan structures and compositions were determined. The glycan structure of peptides from both the constant and variable regions of the monoclonal antibody were determined. FIGS. 2 and 3 show exemplary MS/MS spectra of glycopeptides from the constant and variable regions of the antibody. The overall glycan structure of the individual glycopeptides were determined from the fragmentation pattern of the glycan. A summary of the glycan structures found on the constant and variable regions of the monoclonal antibody analyzed is shown in Table I and II below.

TABLE I

| Fc region glycan structures | Variable region glycan structures |
| --- | --- |

TABLE I-continued

| Fc region glycan structures | Variable region glycan structures |
|---|---|

TABLE II

| Fc region glycan structures | Variable region glycan structures |
|---|---|

What is claimed is:

1. A method of isolating a glycopeptide from a glycoprotein, comprising the steps of:
   (a) chemically or enzymatically cleaving the glycoprotein to generate a mixture of glycopeptides and peptides;
   (b) contacting the mixture with a carbohydrate binding moiety bound to a solid support; and
   (c) isolating the glycopeptides bound to the carbohydrate binding moiety.

2. The method of claim 1, wherein the glycoprotein is an antibody.

3. The method of claim 2, further comprising the step of:
   (d) separating the isolated glycopeptides using high performance liquid chromatography (HPLC);
   (e) calculating the elution times of at least one of the isolated glycopeptides to determine the location of the glycopeptide within the antibody; and
   (f) identifying at least one glycopeptide located within the constant region and/or the variable regions of the antibody based on the elution times.

4. The method of any claim 2, further comprising the step of analyzing at least one isolated glycopeptide by mass spectrometry (MS).

5. The method of claim 4, further comprising the steps of:
   (i) determining the presence of a marker ion indicative of the presence of a glycopeptide and identifying the presence of a glycopeptide, wherein the marker ion includes HexNAc, Hexose, Sialic Acid or Hexose-HexNAc ions; and
   (ii) identifying at least one glycopeptide located within the constant region and/or the variable regions of the antibody based on the presence of the marker ion.

6. The method of any one of claim 4, further comprising the step of determining (i) the location of the glycoslylation site within the antibody, (ii) the heterogeneity of the glycan attached to the isolated glycopeptide, (iii) the glycopeptide mass, and/or (iv) the peptide sequence.

7. The method of claim 1, further comprising:
   (i) the step of reducing and alkylating the glycoprotein before cleaving the glycoprotein;
   (ii) at least one wash step;
   (ii) the step of eluting the glycopeptides from the carbohydrate binding moiety using a molecule that competes with the glycopeptides for binding to the carbohydrate binding moiety; and
   (iii) the step of desalting.

8. The method of claim 1, wherein the carbohydrate binding moiety is a lectin, selected from the group of concanavalin A (ConA), wheat germ agglutinin (WGA), *Aleuria aurantia* lectin (AAL), *Anguilla anguilla* agglutinin (AAA), SNA1 (*Sambucus nigra*), *Helix pomatia* agglutinin, or combinations thereof.

9. The method of claim 1, wherein the glycoprotein is cleaved with trypsin, LysC, GluC, or AspN.

10. The method of claim 7, wherein the competing molecule is methyl mannopyranoside or other buffers with similar properties.

11. A method of determining the location of at least one glycosylation site of an antibody, comprising the steps of:
    (a) reducing and alkylating the antibody;
    (b) chemically or enzymatically cleaving the antibody to generate a mixture of antibody fragments;
    (c) contacting the mixture with a carbohydrate binding moiety bound to a solid support;
    (d) isolating the fragments bound to the carbohydrate binding moiety;
    (e) separating the isolated fragments using high performance liquid chromatography (HPLC); and
    (f) calculating the elution time of at least one of the isolated fragments to determine the location of the fragment within the antibody.

12. The method of claim 11, further comprising the step of determining the location of at least one fragment located within the constant region and/or the variable regions of the antibody based on the elution times.

13. The method of any one of claim 11, further comprising the step of analyzing at least one fragment by mass spectrometry (MS).

14. The method of claim 13, further comprising the steps of:
    (i) determining the presence of a marker ion indicative of the presence of a glycosylated fragment and identifying the presence of a glycosylated fragment, wherein the marker ion includes HexNAc, Hexose, Sialic Acid or Hexose-HexNAc ions; and
    (ii) identifying at least one fragment located within the constant region and/or the variable regions of the antibody based on the presence of the marker ion.

15. The method of any one of claim 13, further comprising the step of determining (i) the location of the fragment within the antibody, (ii) the heterogeneity of the glycan attached to the isolated fragment, (iii) the mass of the glycosylated fragment, and/or (iv) the peptide sequence.

16. A method of characterizing at least one glycosylation site of an antibody, comprising the steps of:
(a) reducing and alkylating the antibody;
(a) chemically or enzymatically cleaving the antibody to generate a mixture of antibody fragments;
(b) contacting the mixture with a carbohydrate binding moiety bound to a solid support;
(c) isolating the fragments bound to the carbohydrate binding moiety;
(d) separating the isolated fragments using high performance liquid chromatography (HPLC); and
(e) calculating the elution time of at least one of the isolated fragments to determine the location of the fragment within the antibody, thereby, characterizing the glycosylation site.

17. The method of claim 16, further comprising the step of determining the location of at least one fragment located within the constant region and/or the variable regions of the antibody based on the elution times.

18. The method of any one of claim 16, further comprising the step of analyzing at least one fragment by mass spectrometry (MS).

19. The method of claim 18, further comprising the steps of:
(i) determining the presence of a marker ion indicative of the presence of a glycosylated fragment and identifying the presence of a glycosylated fragment, wherein the marker ion includes HexNAc, Hexose, Sialic Acid or Hexose-HexNAc ions; and
(ii) identifying at least one fragment located within the constant region and/or the variable regions of the antibody based on the presence of the marker ion within the antibody, thereby, characterizing the glycosylation site.

20. The method of any one of claim 18, further characterizing the glycosylation site by determining (i) the location of the fragment within the antibody, (ii) the heterogeneity of the glycan attached to the isolated fragment, (iii) the mass of the glycosylated fragment, and/or (iv) the peptide sequence.

* * * * *

UNITED STATES PATENT AND TRADEMARK OFFICE
CERTIFICATE OF CORRECTION

PATENT NO.        : 7,820,399 B2             Page 1 of 1
APPLICATION NO.   : 12/152906
DATED             : October 26, 2010
INVENTOR(S)       : Zhigang Wu et al.

It is certified that error appears in the above-identified patent and that said Letters Patent is hereby corrected as shown below:

In the Claims:

Claim 3:
  Column 15, line 53, change "step" to -- steps --.

Claim 4:
  Column 15, line 62, after "The method of", delete "any".

Claim 6:
  Column 16, line 7, after "The method of", delete "any one of".

Claim 13:
  Column 16, line 50, after "The method of", delete "any one of".

Claim 15:
  Column 16, line 63, after "The method of", delete "any one of".

Claim 18:
  Column 18, line 1, after "The method of", delete "any one of".

Claim 20:
  Column 18, line 15, after "The method of", delete "any one of".
  Column 18, line 15, after "further", insert -- comprising --.

Signed and Sealed this
Thirty-first Day of January, 2012

David J. Kappos
*Director of the United States Patent and Trademark Office*